United States Patent
Corbeil

(10) Patent No.: US 12,232,894 B2
(45) Date of Patent: Feb. 25, 2025

(54) DIGITAL DISPLAY FOR A MEDICAL IMAGING SYSTEM BORE

(71) Applicant: Siemens Medical Solutions USA, Inc., Malvern, PA (US)

(72) Inventor: James L. Corbeil, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 203 days.

(21) Appl. No.: 17/997,172

(22) PCT Filed: Jun. 22, 2020

(86) PCT No.: PCT/US2020/070162
§ 371 (c)(1),
(2) Date: Oct. 26, 2022

(87) PCT Pub. No.: WO2021/262242
PCT Pub. Date: Dec. 30, 2021

(65) Prior Publication Data
US 2023/0200758 A1    Jun. 29, 2023

(51) Int. Cl.
*A61B 6/03* (2006.01)
*A61B 6/04* (2006.01)

(52) U.S. Cl.
CPC .............. *A61B 6/032* (2013.01); *A61B 6/037* (2013.01); *A61B 6/04* (2013.01)

(58) Field of Classification Search
CPC ............ A61B 6/032; A61B 6/037; A61B 6/04
See application file for complete search history.

(56) References Cited

U.S. PATENT DOCUMENTS

| | | | |
|---|---|---|---|
| 2007/0244384 A1 | 10/2007 | Gore | |
| 2012/0157758 A1* | 6/2012 | Dietz | A61M 21/02 600/27 |
| 2015/0196367 A1 | 7/2015 | Muller et al. | |
| 2016/0018503 A1* | 1/2016 | Lee | G01R 33/283 324/309 |
| 2016/0058397 A1* | 3/2016 | Kim | A61B 5/055 600/418 |
| 2016/0234486 A1* | 8/2016 | Klaming | A61B 5/055 |
| 2017/0032227 A1 | 11/2017 | Gulaka et al. | |
| 2018/0133518 A1 | 5/2018 | Harper et al. | |
| 2020/0289075 A1* | 9/2020 | Anderson | A61B 6/037 |
| 2021/0166662 A1* | 6/2021 | Wang | A61B 6/4435 |
| 2022/0211272 A1* | 7/2022 | Krueger | G02B 23/26 |

FOREIGN PATENT DOCUMENTS

| | | |
|---|---|---|
| JP | H07327934 | 12/1995 |
| JP | 2012005684 | 1/2012 |
| JP | 2012245315 | 12/2012 |
| WO | 2019173237 | 9/2019 |

OTHER PUBLICATIONS

International Search Report received for Corresponding PCT Application No. PCT/US2020/070162, dated Feb. 17, 2021.

* cited by examiner

*Primary Examiner* — Hugh Maupin

(57) ABSTRACT

A medical imaging system that includes a gantry having an inner bore surface that defines a bore for receiving a patient, wherein a digital display is attached to the inner bore surface of the bore. The system also includes a patient bed for moving the patient into the bore. Further, visual content is displayed on the display that has a calming effect on the patient.

19 Claims, 3 Drawing Sheets

DIGITAL DISPLAY FOR A MEDICAL IMAGING SYSTEM BORE

TECHNICAL FIELD

Aspects of the present invention relate to a medical imaging system, and more particularly, to a medical imaging system that includes a gantry having an inner bore surface that defines a bore for receiving a patient, wherein a digital display is attached to the inner bore surface of the bore for displaying visual content for the patient.

BACKGROUND

Medical imaging systems include a bore that receives a patient to be imaged or scanned. The bore is typically elongated and forms a tunnel that may be imposing or intimidating to those that are either young or for adults who suffer from claustrophobia. This effect is becoming more pronounced as the average bore length of medical imaging systems, such as positron-emission tomography/computed tomography (PET/CT) or magnetic resonance imaging (MRI) systems, is trending longer. Where in the past the typical PET/CT scanner bore cover encompassed the internal componentry necessary to obtain an axial field of view (aFoV) between 160 and 250 mm, there are now scanners with aFoV approaching 1 m or longer. The same holds true of MRIs, where the standard bore cover length is frequently greater than 1.5 mm. In addition to the imposing nature of the scanner, patient/technician interaction is further restricted as the patient is engulfed by the long system, leaving very few options for the technician and patient to interact.

SUMMARY OF THE INVENTION

A medical imaging system for imaging a patient is disclosed. The system includes a gantry having an inner bore surface that defines a bore for receiving the patient, wherein the gantry includes imaging devices for imaging a patient located in the bore. The system also includes a patient bed for moving the patient into the bore. Further, the system includes a digital display attached to an upper portion of the inner bore surface of the bore to enable viewing of the display by the patient along a longitudinal axis of the system.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which.

DETAILED DESCRIPTION

Figure 1:
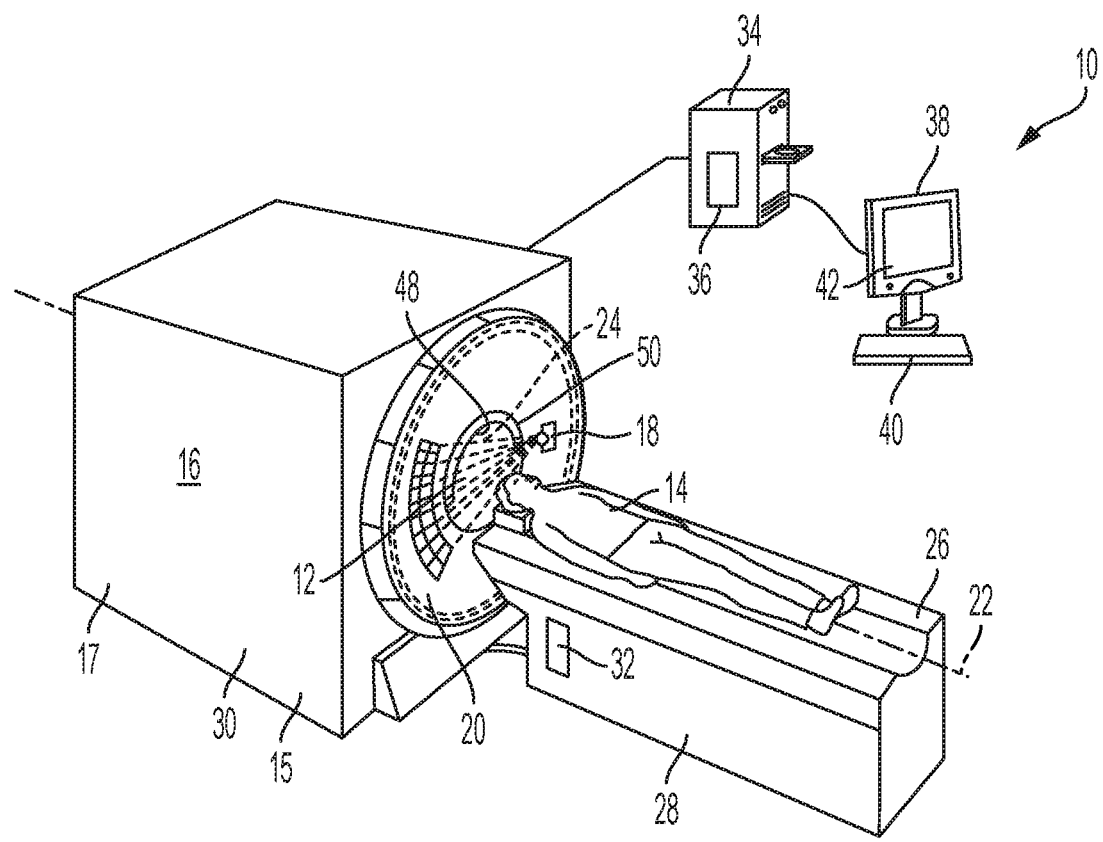
FIG. 1 depicts a medical imaging system in accordance with an aspect of the invention.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Referring to FIG. 1, a view of a medical imaging system 10 in accordance with an aspect of the invention is shown. The invention may be used in conjunction with any medical imaging system 10 having a substantially round shaped bore 12 for receiving a patient 14 such as a magnetic resonance imaging (MRI) system, a positron emission tomography (PET) system, a single-photon emission computed tomography (SPECT) system, a PET/MRI system, an X-ray computed tomography (CT) system, a PET/CT system, a SPECT/CT system and others. For purposes of illustration, the invention will be described in connection with a known PET/CT system 16 having a CT portion 15 and a PET portion 17. The CT portion 15 includes a recording unit, comprising an X-ray source 18 and an X-ray detector 20. The recording unit rotates about a longitudinal axis 22 during the recording of a tomographic image, and the X-ray source 18 emits X-rays 24 during a spiral recording. While an image is being recorded the patient 14 lies on a bed 26. The bed 26 is connected to a table base 28 such that it supports the bed 26 bearing the patient 14. The bed 26 is designed to move the patient 14 along a recording direction through the bore 12 of a gantry 30 of the system 16. The table base 28 includes a control unit 32 connected to a computer 34 to exchange data. In the example shown here the medical diagnostic or therapeutic unit is designed in the form of a system 16 by a determination unit 36 in the form of a stored computer program that can be executed on the computer 34. The computer 34 is connected to an output unit 38 and an input unit 40. The output unit 40 is, for example, one (or more) liquid crystal display (LCD) or plasma screen(s). An output 42 on the output unit 38 comprises, for example, a graphical user interface for actuating the individual units of the system 16 and the control unit 32. Furthermore, different views of the recorded data can be displayed on the output unit 38. The input unit 40 is for example a keyboard, mouse, touch screen or a microphone for speech input.

The bore 12 of the system 10, 16 is defined by a bore inner surface 44 that may include at least one bore cover. The bore 12 extends through the system 16 to form an elongated bore tunnel 46 (FIG. 2) that may be imposing or intimidating to those that are either young or for adults who suffer from claustrophobia. There are design aesthetics that can be employed to lessen the appearance of depth of the bore 12. These include tapering both the bore tunnel 46 and outside shells as the eye progresses backward along the gantry 30. However, this is effective only from certain vantage points and is not effective for a patient 14 inside the bore tunnel 46. Devices such as colorful lights located on medical imaging systems may be used to provide a calming effect on the patient 14. In this regard, the entire disclosure of US Patent Publication No. 2013/0345543A1, published Dec. 26, 2013, to Steibel, J R. et al., is incorporated herein by reference. In addition, music, air flow, clothes placed over the patient's eyes, thematic gantry wraps that serve as a diversion to a patient 14 and other soothing measures or devices may have a calming effect on the patient 14 but provide limited effectiveness. Further, there have been attempts to address the need to stimulate a patient 14 in the bore 12 such as using mirrors on a visor to allow the patient 14 to see projections, screens, light emitting diode (LED) screens on a helmet or a technician residing outside of the scanner. However, such methods are cumbersome and may lead to patient discomfort, set up difficulties, and problems with attenuation correction.

Figure 2:
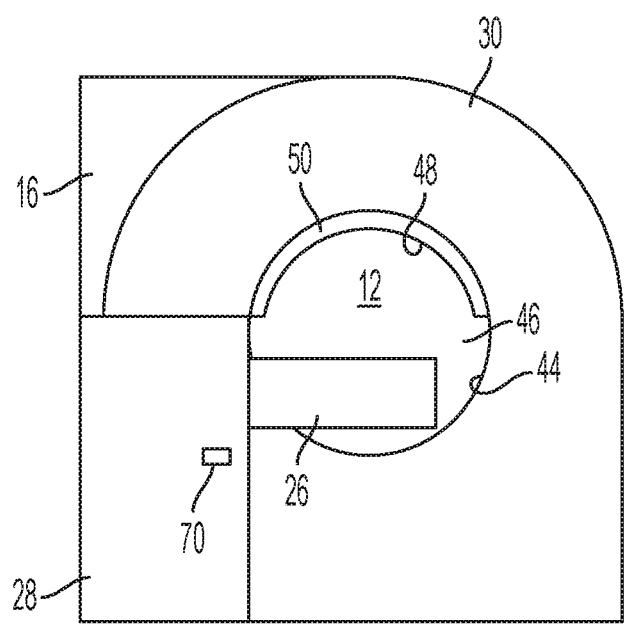
FIG. 2 is a front view of a medical imaging system and depicts a digital display attached to an inner bore surface of a bore in accordance with an aspect of the invention.

Referring to FIG. 2, a front view of an alternate configuration for the system 16 is shown wherein the table base 28 is offset relative to the bore 12. In accordance with an aspect of the invention, a digital display 48 is attached to an upper portion 50 of the bore inner surface 44 such that the display 48 is visible to the patient 14. The display 48 may be a light emitting diode (LED) display 48 fabricated from an array of light emitting diodes (LEDs) or an organic light emitting diode (OLED) display 48 fabricated from an array of OLEDs. It is understood that other types of digital displays may be used. The display 48 may be used to generate both images and text that augment hearing cues in order to provide an enhanced patient experience.

Figure 3:
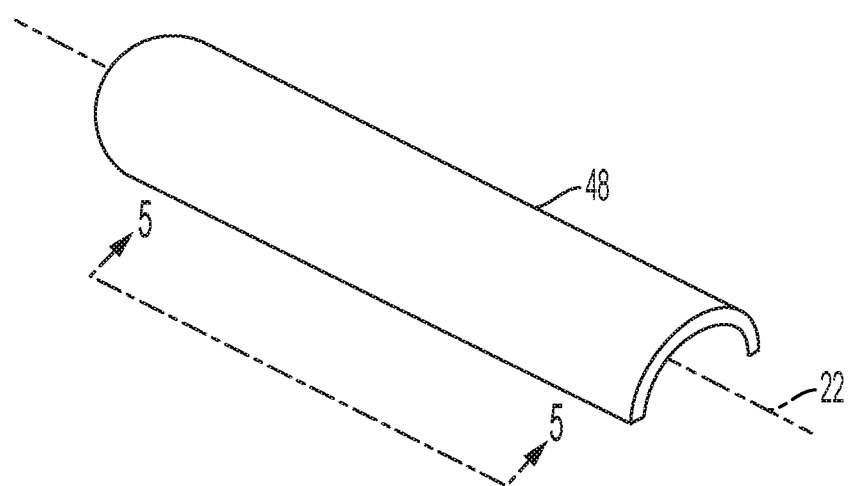
FIG. 3 depicts a configuration for the digital display.

Referring to FIG. 3, a configuration for the display 48 is shown. The display 48 may have a curved or arc shape corresponding to the shape of the bore inner surface 44. In an aspect of the invention, the display 48 has a substantially semicircular shape (i.e. having central angle of approximately 180 degrees) and extends in an axial direction corresponding to the longitudinal axis 22. This enables the display 48 to be visible along a longitudinal axial segment in the bore 12. Alternatively, the display 48 may have a substantially circular shape (i.e. having a central angle of approximately 360 degrees) such that the display 48 covers substantially the entire bore inner surface 44 and has an annular shape. In accordance with an aspect of the invention, other curved or arc configurations may be used having central angles greater or less than 180 degrees. In an embodiment of the invention, the central angle may range between approximately 10 and 180 degrees.

The display 48 may be laminated onto the bore inner surface 44. Alternatively, the display 48 may be printed directly onto the bore inner surface 44 using, for example, a known cylindrical coordinate robot and/or additive manufacturing techniques. Printing the display 48 directly onto the bore inner surface 44, such as a bore cover that forms a part of the bore inner surface 44, subjects the display 48 to lower stress levels thereby improving durability of the display 48. Advantageously, an OLED display 48 provides low attenuation thus operation of the system 16 and the quality of the scan or image is not substantially affected by use of the OLED display 48.

Figure 4:
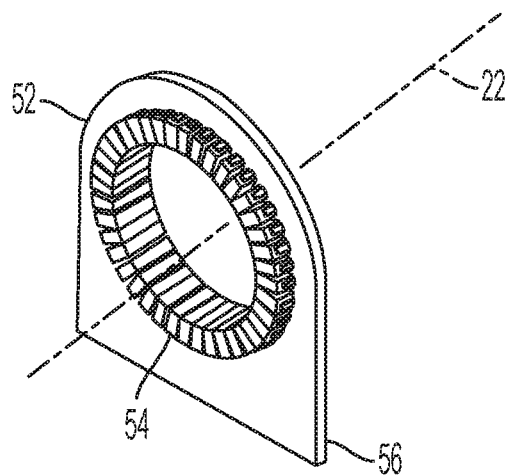
FIG. 4 depicts an exemplary PET detector ring.
Figure 5:
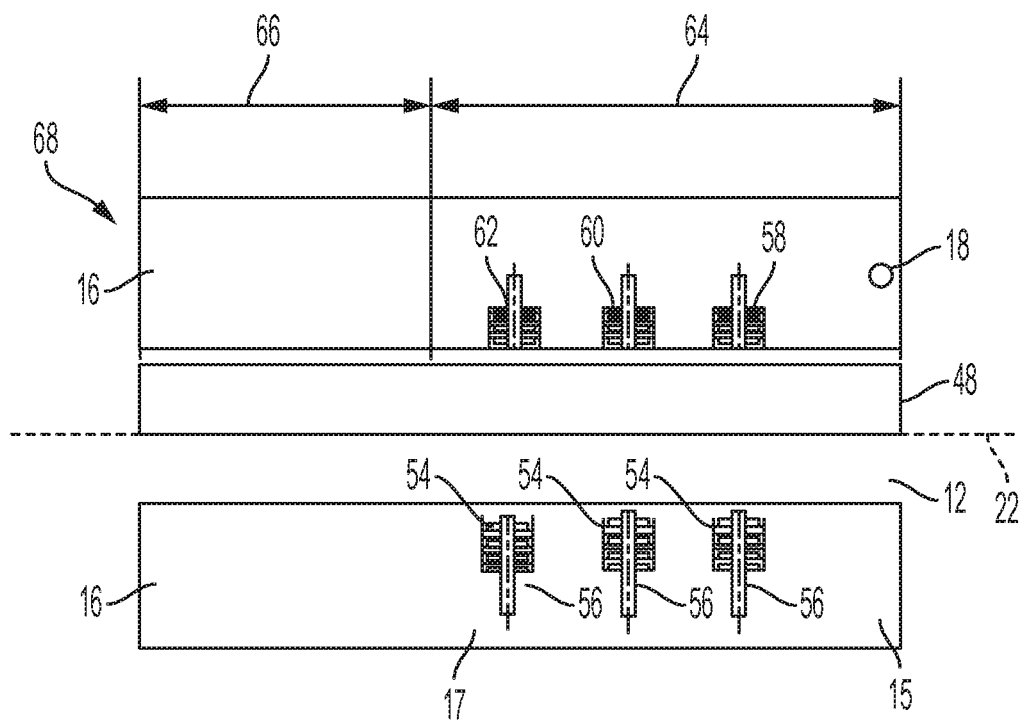
FIG. 5 is a side view of the display along view line 5-5 of FIG. 3 and also depicts a cross-sectional side view of first, second and third PET detector rings and the medical imaging system.

The PET portion 17 of the system 16 includes at least one PET detector ring 52 (see FIG. 4) each including a plurality of known PET detectors 54 arranged in a ring shape configuration on a backplane 56. Referring to FIG. 5, a side view of the display 48 along view line 5-5 of FIG. 3 is shown. For purposes of illustration, a cross-sectional side view of first 58, second 60 and third 62 PET detector rings and system 16 is also shown in FIG. 5. It is understood that more or less than three PET detector rings 58, 60, 62 may be used. The longitudinal axis 22 extends through the PET detector rings 58, 60, 62. The PET detectors 56 define an axial field of view region (aFoV) 64 that extends in the same direction as the longitudinal axis 22. During a known operation of the PET portion 17 of system 16, annihilation events occur in the aFoV 64 wherein an electron interacts with a positron to cause the generation of gamma radiation that is then detected by the PET detectors 56. The detection of gamma radiation is used to generate PET images which are then used in conjunction with CT images generated by the CT portion 15 of system 16 to provide images of a patient or part of a patient's anatomy.

Electronic components associated with a conventional display, such as an OLED display, may be interspersed throughout the display 48. In accordance with an aspect of the invention, electronic components associated with the display 48, such as capacitors, transistors, inductors, integrated circuits and others, that may affect image quality generated by the system 16, are located outside of the aFoV 64 in an electronic component region 66 of the display 48. By way of example, the electronic component region may be located in a rear portion 68 of the display 48. Location of the electronic components outside of the aFoV 64 ensures that the portion of the display 48 within the aFoV 64 provides substantially low attenuation characteristics which do not affect image quality. Alternatively, image artifacts that may be generated due to electronic components located within the aFoV 64 may be corrected using known image artifact correction techniques.

In another embodiment, portions of the display 48 may extend outside of the bore 12 and onto an outside surface of the gantry 30, or a separate display may be located outside of the bore 12, so that the patient 14 is able to view the display 48 as the patient 14 is moved into the bore 12 during imaging. This provides a substantially seamless patient experience as the patient 14 is moved from outside the bore 12 to inside the bore 12 on the bed 26.

Alternatively, the display 48 may be fabricated from a known flexible array of OLEDs to form a flexible OLED display 48. This facilitates installation of the flexible OLED display 48 into the bore 12 and ensures that the shape of the display 48 substantially conforms to the shape of bore inner surface 44. In addition, providing a flexible display 48 facilitates retrofitting existing imaging systems currently in use with a flexible display 48.

In accordance with an aspect of the invention, the display 48 may be used to display visual content and may be personalized by either patient 14 or clinician. In an embodiment, the display 48 may be used to calm the patient 14 or for patient instruction. The display 48 may also be used as a mechanism for stimulation, decoration or clinic advertisement. With respect to calming, the display 48 could be used to display a virtual ceiling so that it appears to the patient 14 that they are looking upward at the ceiling of the room that the patient 14 is in, without obstruction, as the patient 14 moves on the bed 26 along the longitudinal axis 22 from outside the system 16 to inside the bore 12. In addition, colors and images chosen by the patient 14 beforehand (perhaps via a software application), may be displayed during a scan and could be used in conjunction with auditory cues. In an embodiment, the display 48 may be configured to communicate wirelessly with a mobile computing device such as a smartphone. The system 16 may also include a communication interface 70 such as a Universal Serial Bus (USB) port to enable the download or upload of software applications.

The display 48 may also be used as a focusing agent or to entertain the patient 14. For example, an animation or cartoon may be used to draw the attention of a child by flowing across the display 48 and then abruptly stopping, subconsciously enticing the child to perform certain tasks. This activity may be part of a game that would be available in a software application before a scan begins to familiarize the child with the scan procedure such that the scan would be a continuation of the game. Alternatively, the display 48 may display images that are solely entertainment or a real time video feed of a trusted person or a pet that the patient 14 can interact with during the scan. For deaf patients, vocal cues are replaced with visual ones, and researchers would have a new set of tools at their disposal for studies into how the brain works.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

I claim:

1. A medical imaging system for imaging a patient, comprising:
    a gantry having an inner bore surface that defines a bore for receiving the patient, wherein the gantry includes imaging devices for imaging a patient located in the bore;
    a patient bed for moving the patient into the bore; and
    a digital display attached to the inner bore surface of the bore wherein the display includes light emitting elements that generate visual content and wherein the display extends outside of the bore and onto an outside surface of the gantry.

2. The system according to claim 1, wherein the display is located in an upper portion of the inner bore surface to enable viewing of the display by the patient along a longitudinal axis of the system.

3. The system according to claim 2, wherein the display covers approximately 360 degrees of the inner bore surface.

4. The system according to claim 1, wherein the imaging devices define a field of view and electronic components associated with the display are located within the display and outside of the field of view.

5. The system according to claim 1, wherein the system is a positron emission tomography/X-ray computed tomography (PET/CT) system.

6. A method of displaying visual content to a patient positioned in a medical imaging system for imaging a patient, comprising:
    providing a gantry having an inner bore surface that defines a bore for receiving the patient, wherein the gantry includes imaging devices for imaging a patient located in the bore;
    providing a patient bed for moving the patient into the bore;
    providing a digital display attached to the inner bore surface of the bore wherein the display includes light emitting elements that generate visual content and wherein the display has a substantially semicircular shape; and
    displaying visual content to the patient that has a calming effect on the patient.

7. The method according to claim 6, wherein the visual content includes displaying a virtual ceiling on the display so that the patient perceives that they are looking upward at the ceiling of a room when the patient is inside the bore.

8. The method according to claim 6, wherein the visual content includes displaying colors and images chosen by the patient before being imaged and that are displayed during imaging in conjunction with auditory cues.

9. The method according to claim 6, wherein the visual content further includes focusing the patient by displaying a game on the display that familiarizes the patient with a scan procedure.

10. The method according to claim 6, wherein the display is located in an upper portion of the inner bore surface to enable viewing of the display by the patient along a longitudinal axis of the system.

11. The method according to claim 6, wherein the display extends outside of the bore and onto an outside surface of the gantry.

12. The method according to claim 6, wherein the system is a positron emission tomography/X-ray computed tomography (PET/CT) system.

13. A medical imaging system for imaging a patient, comprising:
    a gantry having an inner bore surface that defines a bore for receiving the patient, wherein the gantry includes imaging devices for imaging a patient located in the bore;
    a patient bed for moving the patient into the bore; and
    a digital display attached to an upper portion of the inner bore surface of the bore to enable viewing of the display by the patient along a longitudinal axis of the system and wherein the display extends outside of the bore and onto an outside surface of the gantry.

14. The system according to claim 13, wherein the display covers approximately 360 degrees of the inner bore surface.

15. The system according to claim 14, wherein the imaging devices define a field of view and electronic components associated with the display are located within the display and outside of the field of view.

16. The system according to claim 13, wherein the system is a positron emission tomography/X-ray computed tomography (PET/CT) system.

17. The system according to claim 13, wherein visual content is displayed that has a calming effect on the patient.

18. The system according to claim 17, wherein the visual content includes displaying a virtual ceiling on the display so that the patient perceives that they are looking upward at the ceiling of a room when the patient is inside the bore.

19. The system according to claim 17, wherein the visual content includes displaying colors and images chosen by the patient before being imaged and that are displayed during imaging in conjunction with auditory cues.

* * * * *